(12) United States Patent
Van Bossuyt

(10) Patent No.: US 6,585,969 B1
(45) Date of Patent: *Jul. 1, 2003

(54) NON-VIABLE KERATINOCYTE CELL COMPOSITION OR LYSATE FOR PROMOTING WOUND HEALING

(75) Inventor: Hans Van Bossuyt, Relegem (BE)

(73) Assignee: N. V. Innogenetics S.A. (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/243,333

(22) Filed: Feb. 1, 1999

Related U.S. Application Data

(60) Continuation-in-part of application No. 08/778,031, filed on Jan. 2, 1997, now Pat. No. 5,866,167, which is a division of application No. 08/244,177, filed on Aug. 22, 1994, now Pat. No. 6,126,935.

(30) Foreign Application Priority Data

Nov. 20, 1991 (GB) .............................. 91403137
Nov. 19, 1992 (WO) .............................. PCT/EP92/02657

(51) Int. Cl.$^7$ .......................... A61K 35/12; C12N 5/06; C12N 5/08
(52) U.S. Cl. .................... 424/93.7; 424/520; 424/572; 435/325; 435/366; 435/378; 435/379; 435/380; 435/395; 435/404; 435/405
(58) Field of Search .............. 424/93.7, 520, 424/572; 435/325, 366, 378, 379, 380, 395, 404, 405

(56) References Cited

U.S. PATENT DOCUMENTS

| | | |
|---|---|---|
| 4,016,036 A | 4/1977 | Green et al. ................ 435/347 |
| 4,254,226 A | 3/1981 | Eisinger et al. ............. 435/379 |
| 4,299,819 A | 11/1981 | Eisinger ...................... 424/95 |
| 4,304,866 A | 12/1981 | Green et al. ................ 424/574 |
| 4,443,546 A | 4/1984 | Stemerman et al. ......... 435/387 |
| 4,673,649 A | 6/1987 | Boyce et al. ................ 435/378 |
| 4,888,291 A | 12/1989 | Barrandon et al. ......... 424/93.7 |
| 4,940,666 A | 7/1990 | Boyce et al. ................ 435/371 |
| 4,996,154 A | 2/1991 | Gabriels, Jr. ................ 435/350 |
| 5,130,142 A | 7/1992 | Wong et al. ................ 424/574 |
| 5,273,900 A | 12/1993 | Boyce ......................... 435/402 |
| 5,460,939 A | 10/1995 | Hansbrough et al. ........ 435/1.1 |

FOREIGN PATENT DOCUMENTS

| | | |
|---|---|---|
| EP | 296475 | 12/1988 |
| EP | 364306 | 4/1990 |
| EP | 403139 | 12/1990 |
| EP | 0 215 274 B1 | 2/1993 |

OTHER PUBLICATIONS

Duray, P. et al., "Tissue Culture in Microgravity", *Science & Medicine*, pp. 46–55 (May/Jun. 1997).

Ausubel F.M. et al., "Short Protocols in Molecular Biology," 2nd Edition, pp. 4–11 to 4–12 (1992).

Eisinger, M. et al., "Growth regulation of skin cells by epidermal cell–derived factors: Implications for wound healing," *Proc. Natl. Acad. Sci., USA*, vol. 85, pp. 1937–1941 (Mar. 1988).

Marcelo et al., "Stratification, Specialization, and Proliferation . . . ", *Journal of Cell Biology*, vol. 79, No. 2, pp. 356–370 (Nov. 1978).

Peehl et al., "Clonal Growth of Human Keratinocytes . . . ", *Embase, Excerpta Medica, Amsterdam, NL. Abstract No. 81021358*, (date unknown).

Peehl et al., "Growth and Differentiation of Human Keratinocytes . . . ", *In Vitro*, vol. 16, No. 6 pp. 516–525 (Jun. 1980).

Pittelkow et al., "New Techniques for the In Vitro . . . ", *Mayo Clinic Proceedings*, vol. 61, No. 10, pp. 771–777 (Oct. 1986).

Zyskind et al., "Recombinant DNA Laboratories Manual," pp. 12–17 (1989).

Primary Examiner—David M. Naff
(74) Attorney, Agent, or Firm—Merchant & Gould P.C.

(57) ABSTRACT

Cultures of keratinocyte cells are provided which are free from nonautologous fibroblasts and organ extracts, and which have a high speed of cell amplification for a minimum seeding density. The cultures can be cryopreserved in a buffered isotonic medium containing serum and a cryoprotectant. The cultures are produced by a process that does not involve the use of a feeder layer and organ extracts. A culture medium which can be used contains Medium 199, serum, epidermal growth factor, cholera toxin and/or hydrocortisone, and optionally insulin. A substance for wound healing and for cosmetic applications is derived from cultured human keratinocytes. A non-viable total keratinocyte lysate for use in promoting wound healing is produced by growing keratinocyte cells on a support, detaching the cells from the support, and lysing the detached cells to obtain the lysate which may be frozen and lyophilized. The cells may be grown without using a support to produce the lysate, or to produce a non-viable keratinocyte cell culture lyophilisate or spray dried non-viable keratinocyte cell composition for use in healing wounds.

27 Claims, 3 Drawing Sheets

NON-VIABLE KERATINOCYTE CELL COMPOSITION OR LYSATE FOR PROMOTING WOUND HEALING

CROSS REFERENCE TO RELATED APPLICATION

The present application is a continuation-in-part of U.S. patent application Ser. No.08/778,031, filed Jan. 2, 1997, now U.S. Pat. No. 5,866,167 which is a Division of U.S. patent application Ser. No. 08/244,177, filed Aug. 22, 1994, now U.S. Pat. No. 6,126,935.

BACKGROUND OF THE INVENTION

The invention relates to new cultures of keratinocytes.

The invention also relates to a process for preparing the same.

The invention also relates to the use of new cultures of keratinocytes as wound healing substances.

The invention also relates to pharmaceutical compositions containing as active substances, said new cultures of keratinocytes.

The invention also relates to cosmetic compositions, containing as active substances, new cultures of keratinocytes.

DESCRIPTION OF THE PRIOR ART

Skin is presumably the organ most subject to injury. Skin repair is a complex process that can be divided in 4 phases usually described as inflammation, granulation tissue formation, epithelialization and remodeling of the connective tissue matrix. Each of these phases is complex in itself, and it is clear that for good wound healing, the processes must occur successively and in coordination. Good wound healing can be defined as restoration of the skin, including the dermal and epidermal part, in such a way that the resulting scar tissue maximally resembles the unwounded skin structurally, histologically, functionally, and esthetically obviously, such scar tissue is different from a hypertrophic scar or keloid.

For purposes of clarity a simplified description of the composition of human skin is given below. The upper part is composed of the epidermis, which contains mostly keratinocyte or epithelial cells, some melanocytes and Langerhans cells, and several Merkel cells. Five different layers are found in the epidermis, reflecting the state of keratinization. The proliferating keratinocytes at the base of the epidermis, i.e., in the stratum basal, are attached to the dermis via the basement membrane. The dermis is composed of connective tissue, including fibroblasts and other connective tissue cells, and connective tissue matrix substances. Blood vessels, nerves, sensory organs, sweat glands, sebaceous glands, and hair follicles are present in the dermis.

Clinical and animal experiments have demonstrated that application of in vitro cultured (human) keratinocytes, for instance as sheets, induces wound healing in chronic wounds such as ulcers and in burns, which may be treated concomitantly with meshed split skin autografts. Moreover, there are indications that the application of cultured keratinocyte grafts suppresses hypertrophic scar formation and keloid formation. Initially, autografts were used, which were prepared by growing keratinocytes isolated from the patients own skin. Confluent (differentiated) keratinocyte cultures are then detached from the culture dish and applied as a sheet, with basal cells facing downwards on the wound. About 3 weeks are needed before a reasonable amount of keratinocytes can be cultured for application as an autograft. Even then, the amount may not be sufficient to cover the entire wound surface. However, this time period may be critical for the patient, especially in the case of extensive third degree burns.

Therefore, experiments were undertaken to apply keratinocyte allografts. Keratinocytes are isolated from the skin of one person, cultured to obtain confluent keratinocyte sheets, and then applied on the wound of a patient. No differences in wound healing activity were observed between auto- and allografts. A main disadvantage of cultured allografts is the risk of transferring pathogens such as human immunodeficiency virus, hepatitis B virus, and cytomegalovirus, from the skin donor to the acceptor patient.

These techniques for wound treatment make use of fresh keratinocyte grafts, containing proliferating keratinocytes. The keratinocyte sheets are detached from the culture vessel by treatment with Dispase and immediately applied onto the wound. The availability of these sheets in terms of time and quantity is a major drawback of fresh keratinocyte grafts. It is assumed that proliferating keratinocyte cultures contain higher wound healing activity than more differentiated cultures. Moreover, only a multilayer culture can be detached as a sheet from the culture vessel, and can be spread over the wound. Therefore, cultured keratinocytes have to be taken at an optimal growth phase. However, it is impossible to predict when a patient will enter the hospital and how many keratinocyte grafts will then be needed. Another drawback of using fresh (autologous) keratinocyte sheets is that a certain period of time is still required before a sufficient amount of keratinocyte sheets can be grown and then applied.

Cryopreserved allografts partially circumvent these inconveniences. Cryopreserved keratinocyte grafts can be prepared as follows: confluent (differentiated) keratinocyte cultures are rinsed with phosphate buffered saline (PBS), cultured for 1 day without additives (epidermal growth factor, insulin, cholera toxin, triiodothyronin, transferrin, hydrocortisone), detached from the dish by treatment with Dispase and adhered to a transfer substrate (e.g., Interfaces Wuhrlin-Soplamed). The sheets are soaked in culture medium supplemented with 10% DMSO as cryoprotectant, and stored frozen in liquid nitrogen or for a shorter period of time at −60° C. Before application, the specimen is thawed and rinsed with PBS in order to remove DMSO and bovine serum proteins. The sheets are applied with basal cells facing downwards as fresh sheets. After thawing, about 60% of the cells are viable as judged from vital staining.

Initially, it was assumed that the keratinocytes from cultured allografts remain and grow on the wounds, an event which is clinically known as "take". However, several reports recently demonstrated that wound closure is due to growth.of host epithelium.

Thus, healing is induced without permanent take of keratinocyte grafts, suggesting that the wound healing activity may be due to a (chemical) substance(s) associated with the cultured keratinocytes, which stimulates keratinocyte outgrowth. Consequently, it would not be necessary to apply sheets of viable keratinocytes. Therefore, the cultured keratinocyte sheets were lyophilized and the wound healing activity was compared with fresh and cryopreserved sheets.

Hence, the beneficial effect of cultured keratinocyte sheets in wound healing can probably be attributed to (a) substance(s) present in the cultured keratinocyte or induced by (a) molecule(s) present in the cultured keratinocytes. To date the(se) factor(s) and their concentration in the cultured keratinocytes are unknown. It cannot be excluded that certain known cytokines and growth factors are present. Many known growth factors, e.g., fibroblast growth factor (FGF), platelet derived growth factor (PDGF), epidermal growth factor (EGF), transforming growth factor alpha (TGF-α), transforming growth factor beta (TGF-β), influence keratinocytes and skin fibroblasts. For instance, TGF-β, EGF, and FGF induce keratinocyte proliferation. TGF-β and PDGF stimulate the synthesis of collagen and other connective tissue components. Vascularization can be influenced by basic-FGF and TGF-α. Because of these properties, such growth factors may play a role in wound healing.

Clinical results showed that fresh and cryopreserved cultured keratinocyte sheets stimulate re-epithelialization, resulting in quicker healing compared to classic wound treatment or application of meshed split skin autografts only. According to the results of our animal model for wound healing, lyophilized cultured keratinocytes gave better results than keratinocyte sheets.

The term "lyophilized keratinocytes" denotes the product obtained from human or animal keratinocytes, which have been grown in vitro to the subconfluent, confluent, or differentiated state, and then a lyophilisate is prepared of these cells in such a way that no or minimal degradation of cell-associated substances occurs. Such a lyophilisate contains wound healing activity. Cell extracts from these cultured keratinocytes also contain wound healing activity. A cell extract may be prepared, for instance, after lysis and/or disruption of the cultured keratinocytes and subsequent fractionation. The total material or separate fractions may be lyophilized. Lyophilization is not necessary, but it is advantageous in that the resulting substance is easier to store, can be kept in a small place, is easier to handle, can be applied in a formulation (e.g., in a dry powder, an ointment, a suspension, a solution, a gel, a creme or a biocompatible, synthetic or natural solid matrix) chosen according to the circumstances, can be administered at an optimal dose, normally has a longer shelf life, and can easily be screened for the most active preparation.

One advantage of lyophilized cultured keratinocytes is that the material is readily available exactly at the moment it is needed, in contrast to fresh cultured keratinocyte sheets. Before application on a wound, fresh keratinocyte sheets have to be cultured for one day without fetal calf serum and additives such as epidermal growth factor, cholera toxin, triiodothyronin, transferrin, etc. Subsequently, the sheets have to be removed from the culture dish with Dispase, rinsed and transferred to the operating room in a sterile manner. In the case of cryopreserved sheets, the storage medium, containing 10% DMSO as a cryoprotectant, is thawed as quickly as possible at 37° C. and thoroughly rinsed with PBS before it is transferred to the operating room. Thawed cryopreserved keratinocyte grafts have to be handled carefully since the sheets are extremely fragile. Besides the need for specialized accommodations, it takes at least 1 day for fresh keratinocyte grafts and about 1 h in the case of cryopreserved keratinocyte grafts, before they can be applied on the wound. In contrast, lyophilized keratinocyte material is instantly available and may be applied as such, or rehydrated in a previously prepared sterile gel or salt solution. Lyophilized-keratinocyte derived substances may be applied at the optimal dose. In the case of keratinocyte sheets, the wound is covered with a sheet and it is assumed to be useless to put another sheet on top.

Interdonor differences play a role in the activity of the cultured keratinocytes. The keratinocyte proliferation stimulating activity of lyophilized keratinocyte-derived substances is easily tested in vitro. The most active batches can be selected for patient treatment. Fresh keratinocyte grafts cannot be tested and, in the case of cryopreserved keratinocyte sheets, the preparation of the material requires additional work.

Lyophilized cultured keratinocytes, extracts or fractions are easy to store. A large amount may be prepared beforehand. Another advantage is that keratinocyte growth stimulatory activity may be tested in vitro in order to select the most active preparations. This is obviously impossible when fresh keratinocyte sheets are used. Moreover, fresh sheets must be used at an optimal time and may not be stored at all. If there are no patients to treat at that optimal moment of culture, the cells become worthless for this purpose. Besides, cryopreserved keratinocyte sheets should be stored in a cryobiological storage vessel containing liquid nitrogen. The stock of lyophilized keratinocytes can be kept at −20° C. as dry powder.

Lyophilized keratinocytes do not require special transportation facilities. By contrast, when detached from the culture surface, fresh and cryopreserved keratinocyte grafts have to be transported in isotohic, sterile buffered medium to prevent drying of the keratinocytes. Moreover, these keratinocyte grafts may detach from the supporting gauze, and start to float or curl up, hampering the exact method of application, i.e., basal keratinocytes facing downwards. Lyophilized keratinocyte material is a light weight powder, simply kept in a sterile vial. It is recommended to rehydrate and/or redissolve the powder in gel or saline prior to use. The preparation can then be kept for at least 1 week at 4° C. without loss of keratinocyte proliferation stimulating activity. Rehydrated substance may have better contact with the wounded tissue, thereby favoring the healing process.

Since the substance is completely dry during storage, proteinases are not active, thus increasing the shelf life.

Some cultures of keratinocytes which are used either for skin grafting, wound healing or for fundamental studies require cultures containing fibroblasts, such as 3T3.

For instance, the document titled "Serial cultivation of strains of human epidermal keratinocytes: the formation of keratinizing colonies from single cells" (J. G. Rheinwald et al., Cell, vol. 6, pp. 331–344, November 1975) describes the presence of fibroblasts to initiate colony formation of human epidermal keratinocytes, but states that proliferation of fibroblasts must be controlled so that the epidermal cell population is not overgrown. Both conditions can be achieved by the use of lethally irradiated 3T3 cells at the correct density.

Another example where 3T3 cells are used is the culture of keratinocytes described in "Growth of cultured human epidermal cells into multiple epithelia suitable for grafting" (H. Green et al., Proc. Natl. Acad. Sci. USA, vol. 76, no 11, pp. 5665–5668, November 1979).

In order to avoid the use of neoplastic cells, i.e., the 3T3 fibroblasts, in cultures for application on open wounds, several reports have described feeder layer-free keratinocyte culture techniques. Feeder layer-free keratinocyte cultures have been performed on special substrates (e.g., on fibronectin (Gilchrest B. A. J. Cellular Physiology, 1982) or collagen-coated substrates (Hawley-Nelson P. J. Invest. Dermatol., 1980)) or the cells were plated at higher densities on an uncoated surface of culture plastic (Eisinger M. PNAS 1979).

Some authors have proposed to cultivate keratinocytes on media which are free from fibroblasts, but which contain bovine pituitary extracts or bovine brain extracts.

More precisely, Mark R. Pitellkow et al. have disclosed in "New techniques for the in vitro culture of human skin keratinocytes and perspectives on their use for grafting of patients with extensive burns" (Mayo Clinic Proceedings, vol. 61, pp. 771–777, 1986) a culture method involving a two-phase technique: proliferation (phase 1) and differentiation (phase 2). Phase 1 is performed in medium without serum and in standard tissue flasks without mesenchymal cell feeder layers.

The culture medium used for phase 1 is designated complete MCDB 153 and consists of epidermal growth factor, insulin, bovine pituitary extract, ethanolamine, phosphoethanolamine, and hydrocortisone.

Phase 2 involves culturing of keratinocytes in Dulbecco's modified Eagle medium that contains serum, thereby facilitating cell stratification and differentiation.

B. A. Gilchrest et al. describe in "Attachment and growth of human keratinocytes in a serum-free environment" (Journal of Cellular Physiology, vol. 112, pp. 197–206, 1982) a culture medium for keratinocytes containing bovine brain extracts. In this document, there is no mention of wound healing properties.

However, these culture media (of Pittelkow et al. and of Gilchrest et al., see above) contain bovine pituitary extracts or bovine brain extracts, which implies:

that said media are not standardized;

that confluency is reached only with difficulties; and that special substrates may be required.

Media containing no fibroblasts and no bovine organ extract have also been developed.

C. L. Marcello et al. have in their publication entitled "Stratification, specialization, and proliferation of primary keratinocyte cultures" (J. Cell. Biology, vol. 79, pp. 356–370, November 1978), described the culture of mouse keratinocytes in a medium containing Medium 199 and fetal calf serum. The culture temperature ranges between 32–33° C. In this process, the seeding density is high ($2 \times 10^5$ cells/cm$^2$) and confluence is reached in 4–6 weeks. The drawback is that this process results in low yields of keratinocyte sheets. In this document, there is no mention of wound healing properties.

Y. Kitano et al. in "Growth of human keratinocytes in a defined medium supplemented with growth factor of serum" (Dermatologica, vol. 180, pp. 236–239, 1990) have described that the cultures of keratinocytes were started by inoculating the keratinocytes suspended in Eagle's minimal essential medium supplemented with 20% fetal bovine serum, except for the experiments related to cell attachment. The basal medium consisted of equal volumes of Iscove's medium and Ham's F-12 medium supplemented with insulin, transferrin, ethanolamine, selenite, hydrocortisone and epidermal growth factor. The salting out of bovine serum was then performed in a conventional manner to fractionate bovine serum. In this document, there is no mention of wound healing properties. It is not clear from this article whether confluency is reached, which makes the cultured cells inappropriate for wound healing.

M. Eisinger et al. have described in "Human epidermal cell cultures: Growth and differentiation in the absence of dermal components or medium supplements" (Proc. Natl. Acad. Sci. USA, vol. 76, No. 10, pp. 5340–5344, October 1979), the human epidermal cell growth and differentiation in vitro, provided that the pH was 5.6–5.8, the seeding density was $2.5 \times 10^5$ cells and the temperature was maintained at 35–37° C.

The medium contained Eagle's minimal medium plus nonessential amino acids, 2 mM L-glutamine, hydrocortisone at 0.4 $\mu$g/ml, 10% fetal bovine serum, penicillin, streptomycin and FUNGIZONE®. It takes 3 to 6 weeks before the confluent cultures (that can be used for preparation of cell extracts) are obtained. The drawbacks are the necessity of high seeding density and the slow growth of the cell cultures.

P. Hawley-Nelson et al. have described in "Optimized conditions for the growth of human epidermal cells in culture" (The Journal of Investigative Dermatology vol. 75, pp. 176–182, 1980) methods to optimize the growth of human keratinocytes in the following media: CMRL 1066, Dulbecco's MEM with nonessential amino acids, Eagle's MEM with nonessential amino acids, Eagle's MEM with nonessential amino acids with D-valine substituted for L-valine, and BGJ$_b$ Fitton-Jackson modification. Two custom media were also tested: a modification of Eagle's MEM with 4-fold higher amino acids and vitamins (Fusening NE, Worst PKM: Mouse epidermal cell cultures. II. Isolation, characterization and cultivation of epidermal cells from perinatal mouse skin. Exp Cell Res. 93:443–457, 1975), and a modification of Waymouth's MB752/1 with added nonessential amino acids, putrescine, insulin, pyruvate, arginine, hydrocortisone and epidermal growth factor (Steele V E, Marchok A C, Nettesheim P., Transformation of tracheal epithelium exposed in vitro to N-methyl-N'-nitro-N-nitrosoguanidine (MNNG). Int J. Cancer 20:234–238, 1977).

Primary epidermal cells grew to confluency within 2 weeks for plating inputs of $10^5$/cm$^2$.

Moreover, epidermal growth factor exposure resulted in the rapid appearance of a cell type which lacked the characteristic keratinocyte morphology and proliferated rapidly. Because the origin of these cells has not yet been determined, epidermal growth factor was not used further. In the above-mentioned article, these is no mention of wound healing properties.

SUMMARY OF THE INVENTION

The aim of the present invention is to provide cultures of keratinocyte cells which are free from nonautologous fibroblasts and free from organ extracts.

Another aim of the invention is to provide cultures of keratinocyte cells characterized by a high speed of cell amplification for a minimum seeding density.

Another aim of the invention is to provide confluent and cohesive keratinocyte sheets which can be used for their wound healing properties.

Another aim of the invention is to provide a process for preparing a culture of keratinocyte cells to obtain the above-mentioned culture cells.

Another aim of the invention is to provide a process for the culture of keratinocytes which does not involve the use of a feeder layer and organ extracts.

Another aim of the invention is to provide a medium which enables obtention of the above-mentioned culture of keratinocyte cells.

Another aim of the invention is to provide a total cell lysate and cell fractions derived from cultures of keratinocytes,.

Another aim of the invention is to provide a wound healing substance derived from cultured human keratinocytes.

Another aim of the invention is to provide a substance derived from cultured human keratinocytes which can have cosmetic applications.

This picture clearly shows the presence of rete ridges and the different cell layers in the epidermis (stratum basale, stratum spinosum, stratum granulosum, stratum corneum).

It also shows that there is no detachment between epidermis and dermis and it also shows the presence of collagen bundles in the pars reticulare of the dermis (lower part of the picture). Blood capillaries in the dermis are ordered in groups.

Figure 1:
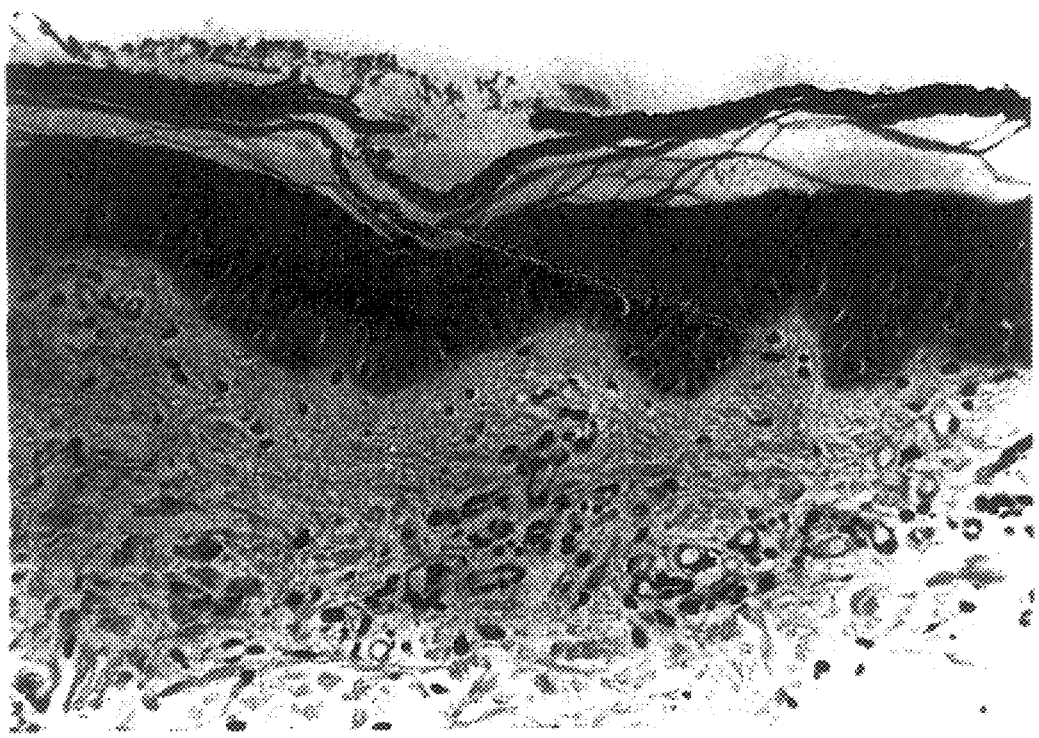
FIG. 1 represents the unwounded pig skin (magnification: 900×).
Figure 2:
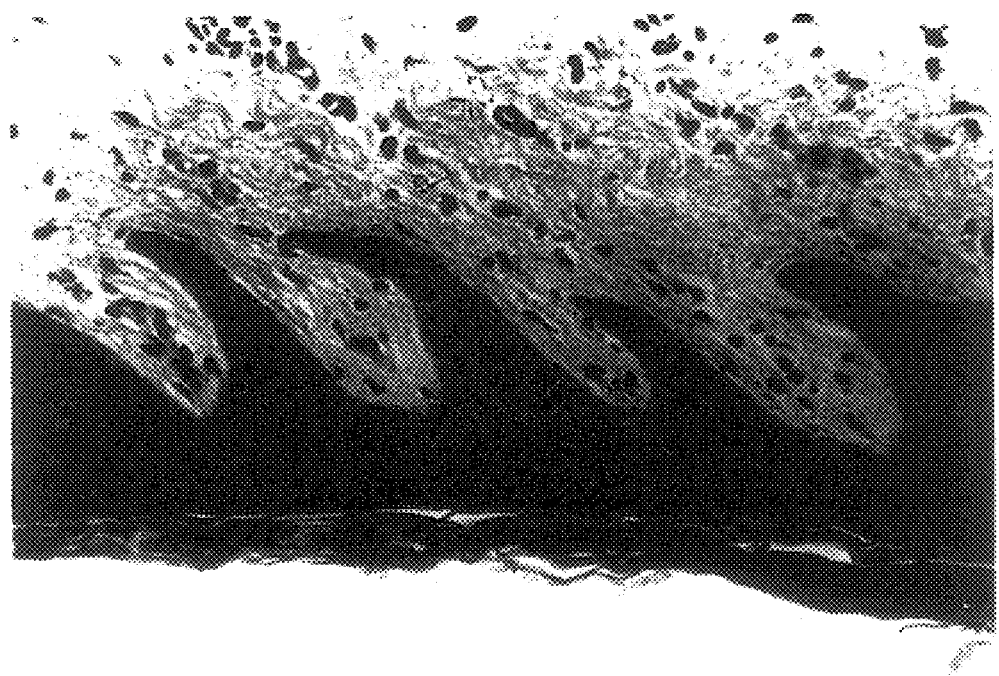

FIG. 2 represents scar tissue in the pig skin 91 days after wounding. Until wound closure, the wound was treated with lyophilized cultured keratinocytes of the invention. The picture shows the presence of rete ridges, the attachment between epidermis and dermis and the presence of collagen bundles. It also shows the presence of thin collagen bundles. The epidermis contains the different cell layers. Magnification: 900×.

Figure 3:
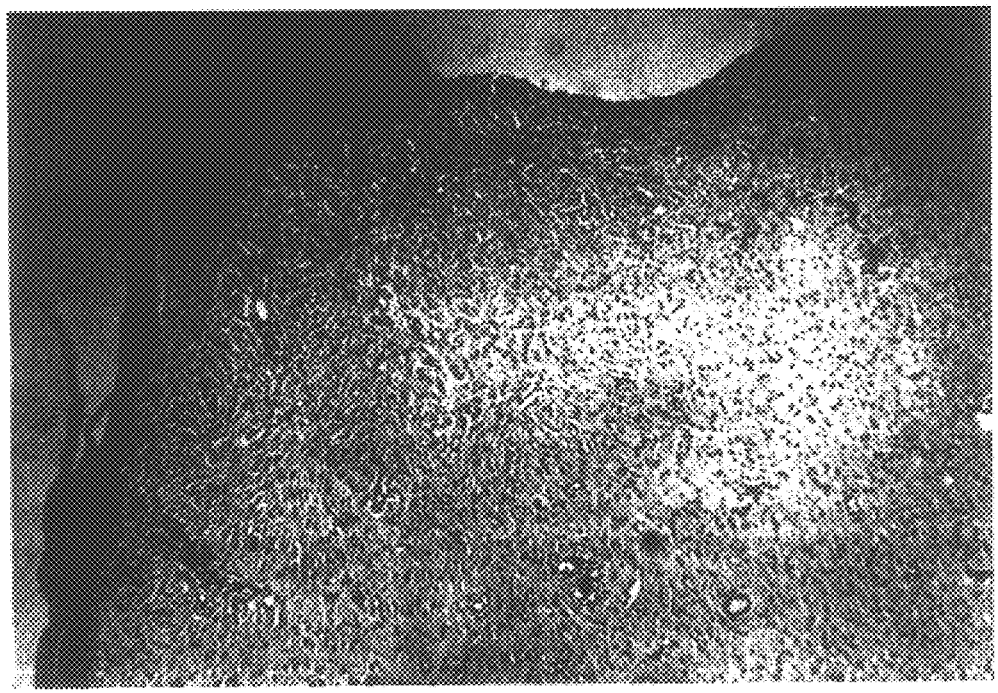

FIG. 3 represents a lower magnification (magnification: 200×) of pig skin, 84 days after wounding and treated with Duoderm® until wound closure.

This picture shows that there are no rete ridges and that there is detachment between epidermis and dermis. Collagen bundles and blood capillaries cannot be evaluated on this picture because of the low magnification.

DESCRIPTION OF THE EMBODIMENT

The invention relates to cultures of keratinocyte cells which are free from nonautologous fibroblasts, free from organ extracts, particularly pituitary extracts, and free from large flat translucent keratinocyte cells, which have a speed of cell amplification of at least 1 cellular division every 2 days, particularly of at least 1 division every 2.5 days, preferably for a minimum seeding density of $1\times10^4$ cells/cm$^2$, preferably of 3 to $5\times10^4$ cells/cm$^2$.

"Organ extracts" designate bovine brain extracts, and more particularly pituitary extracts.

The large translucent keratinocyte cells are flat atypical epithelial cells characterized by filamentous cytoplasm.

"Large" in the expression "large flat translucent keratinocyte cells" means that from observations made in the inverted light microscope, the cells occupy about 3–6 times greater surface area in the culture than the normal size of keratinocytes in the culture medium of the invention or than the majority of keratinocytes in the epidermal growth factor containing cholera toxin-free culture.

"Flat" in the expression "large flat translucent keratinocyte cells" means that the cells can be recognized as being less thick than the normal keratinocytes obtained in the culture of the invention. Thickness means focal thickness in the microscope.

"Translucent" in the expression "large flat translucent keratinocyte cells" means that the cytoplasm is less dense under the light microscope than are keratinocytes obtained in the culture medium of the invention. In other words, when there is more than about 75% of light which comes through the cell, it is a translucent cell. When there is less than about 50% of light coming through the cell, it is a normal keratinocyte cell.

The method for determining the speed of cell amplification is given hereinafter.

For example, 100 cells are seeded in a culture medium of the invention, as defined hereinafter. All 100 are viable as judged from the trypan blue viability test (i.e., viable cells exclude the stain, but dead cells are unable to do so and are therefore stained blue). Only a certain percentage of the seeded cells will attach and spread. These two latter phenomena, attachment and spreading, are prerequisites for cell division. Attachment is the phenomenon whereby cells settle from a suspension, and attach onto the support. The cells still maintain a round shape at this moment. Spreading then occurs: round cells may become flattened and then attach over a larger surface onto the support. Subsequently, cells may divide, i.e., multiply. One mother cell gives rise to 2 daughter cells. This process is called mitosis.

Proliferation or multiplication may proceed, and the support area will be filled with cells. At that moment, the culture is called confluent.

The speed of cell amplification means the cell population doubling time.

The method for measuring cell amplification is as follows: Five$\times10^4$ trypan blue-excluding cells are seeded per cm$^2$ in 6 dishes of 35 mm in diameter. After 3 days (i.e., on day 3) (all cells that were able to attach have then had the chance to attach), three culture dishes are rinsed to remove the floating, non-attached cells. The attached cells do not divide yet at this moment. They are removed from the culture dish by trypsin-EDTA treatment (just as for the preparation of subcultures) and counted in a hemocytometer under the light microscope. Hence, the total amount of attached cells is known. For example, for the three dishes, a mean of 50,000 cells per dish might be obtained. When the 3 other cultures reach confluency after 13 days (i.e., on day 13), the cultures are rinsed to eventually remove floating cells. The attached cells are then removed by trysin-EDTA and counted as above. A mean of $1.2\times10^6$ cells per dish is obtained. It is known that 1 cell divides into 2 cells. That gives: 50,000→100,000→200,000→400,000→800,000 and 1/2 division from 800,000→1,200,000. Thus, 4.5 divisions occur from confluency (day 13) to the day on which all cells that were able to attach, have attached (day 3), i.e., 4.5 divisions in 10 days, which corresponds to one division per 2.2 days.

If the density is lower than $1\times10^4$ cells/cm$^2$, the growth of the cells may be such that confluency might not be reached.

If the density is higher than $5\times10^4$ cells/cm$^2$, confluency is reached more rapidly.

In a preferred embodiment of the invention, the culture contains no more than about 10%, preferably no more than about 7% of autologous non-keratinocyte cells such as star-shaped, non-keratinocyte cells, and contains no more than about 1%, and preferably no more than about 0.5% of autologous fibroblasts.

According to an advantageous embodiment of the invention, the culture contains no autologous fibroblasts and no autologous non-keratinocyte cells, and particularly no autologous melanocytes and no autologous Langerhans cells.

The proliferation rate (i.e., cellular division rate) of keratinocytes is reduced in the presence of non-keratinocyte cells such as melanocytes and/or Langerhans cells. This is a concentration-dependent effect. The attached cell population may consist of no more than 10% of these cells. However, a confluent keratinocyte layer will undoubtedly be obtained. These non-keratinocyte cells are star-shaped cells and play a minor role in keratinocyte subcultures, since most do not spread after passage in the system of the invention.

The star-shaped, non-keratinocyte cells are, for instance, melanocytes and Langerhans cells.

If the culture contains more than about 10% of autologous non-keratinocyte cells, there is an apparent inhibition of keratinocyte cell division at the beginning of the culture (for instance, during the first week).

After seeding, the cultures should not contain more than about 1% of autologous fibroblasts of the total amount of spread cells, because no confluent keratinocyte sheet is obtained if a larger amount of fibroblasts contaminates the initiated culture. If the amount of autologous fibroblasts is higher than about 1%, the culture surface is covered with a monolayer consisting of areas of fibroblasts and islands of keratinocytes, which leads to non-cohesive cell sheets.

According to another preferred embodiment of the invention, the culture of the invention is such that the keratinocyte cells are confluent and locally differentiated about 10 days after the start of the culture of keratinocytes seeded at a density as low as $1 \times 10^4$ cells/cm$^2$, but preferably at 3 to $5 \times 10^4$ cells/cm.

The expression "confluent" indicates that the entire surface of the culture vessel is covered by cells. The majority of the cells in such culture have been actively proliferating (i.e., dividing). However, in the case of keratinocytes in the culture of the invention, it is not excluded that cell differentiation occurs in certain areas of the culture, even before confluency.

As to "differentiation", it is recognized when keratinocytes containing kerato-hyaline granules are found in the culture. Kerato-hyaline granules are detected as follows. Kerato-hyaline granules are recognized in hematoxilin-eosin stained histologic sections of cultured multilayered keratinocyte sheets. The granules are seen as brown spots in the light microscope. Once the culture surface is filled with keratinocytes, i.e.) confluency is reached, the cells proliferate further resulting in thicker, multilayered sheets. The cells in the upper layers are thus differentiated.

"Locally differentiated" means that the differentiation has occurred in certain areas of the culture, even before confluency.

In a preferred embodiment of the invention, the cells must not be overly differentiated. This is because the culture must be strong enough to be able to be detached from the support as a sheet, and this requires a multilayered cohesive culture. Such a multilayered cohesive culture contains many keratinocyte cells with kerato-hyaline granules and is, therefore, differentiated.

"Cohesive" means that the cells remain attached together.

The term "sheet" refers to a confluent keratinocyte culture, fresh or cryopreserved, which is detached intact from the culture dish or by Dispase treatment and which can be applied on the wound of a patient, either immediately in the case of fresh keratinocyte sheet or upon thawing in the case of a cryopreserved sheet. A preferred type of sheet is a cryopreserved keratinocyte graft which can be prepared as described above.

It is appropriate in making a sheet to use keratinocyte cell cultures that are not white and that do not contain bubbles everywhere, which are characteristics of an "overly differentiated stage". When the sheets are too differentiated, there might almost be no proliferation in the culture, and furthermore, the wound healing properties might be less optimal. When the sheets are too differentiated, they can be detached from the support without enzyme, whereas when the confluent sheets are less differentiated, it is necessary to use an enzyme such as Dispase (obtained, for instance, from Boehringer Mannheim).

According to a preferred embodiment of the invention, the culture of keratinocyte cells can be subcultured at 8 passages, and preferably 6 passages, without loss of differentiation, with a split ratio of 1/4 to 1/2, preferably of 1/3.

It is to be recalled that a subculture is a mother culture from which a first derived culture is carried out by trypsinization (to remove cells from the support and separate cells which are attached together to obtain a suspension of separate cells), and seeding the suspended cells on X dishes (X defined afterwards), from said derived culture, a second derived culture is carried out, with the total number of derived cultures representing the number of subcultures.

The expression "split ratio" of 1/X refers to the fact that, from the totality of a mother culture, it is possible to seed and obtain confluency and differentiation on X Petri dishes.

The invention also relates to the culture of keratinocytes such as that obtained by a process comprising the following steps:

seeding keratinocyte cells on a support at a density as low as $1 \times 10^4$ cells/cm$^2$, preferably of 3 to $5 \times 10^4$ cells/cm$^2$ in a culture medium containing a basal medium, itself containing Medium 199, with the following additives: serum, epidermal growth factor, hydrocortisone and/or cholera toxin, and possibly insulin, free from non-autologous fibroblasts, and free from organ extracts, particularly pituitary extracts; and growing such cells at a temperature of 37° C. in a water-saturated atmosphere containing $CO_2$, preferably in the range of about 1% to about 10%, more particularly in the range of about 2% to about 8%.

The invention also relates to cultures of keratinocytes according to the invention in a lyophilized form.

The invention further relates to extracts of keratinocyte cultures according to the invention, possibly in lyophilisate form. Such extracts can be formed in a conventional manner from the cultures.

The term "extract" refers to a cell product obtained from human or animal keratinocytes which has been grown in vitro to confluency and which has retained its wound healing activity. A cell extract can be prepared, for instance, after lysis and/or disruption of the cultured keratinocytes and subsequent fractionation, and the different fractions can be lyophilized as described above. Such lyophilisates can be applied as a dry powder, in an ointment, in a suspension, in a solution, in a gel, in a creme or in a biocompatible, synthetic or natural, solid matrix, chosen according to the circumstances and administered in an optimal dose.

The invention still further relates to a pharmaceutical composition containing, as an active substance, a culture or extract as defined above, which is preferably in lyophilized form and which can be used to promote the healing of surface wounds, for example of skin, such as human skin. This pharmaceutical composition preferably comprises the lyophilized culture or extract in a formulation suitable for application onto surface wounds. Such a formulation can be applied directly to a surface wound either as a dry powder or in the form of a gel, a creme, an ointment, a suspension, a solution, or a biocompatible, synthetic or natural solid matrix, any of which can be prepared in a conventional manner, if desired with conventional, pharmaceutically acceptable excipients and additives. Normally, the lyophilized culture or extract is incorporated in such a composition in a concentration that depends on of the type of surface wound to be healed and the circumstances, under which the composition is to be used. For instance, a lyophilized culture or cell extract of this invention can be applied at a concentration, such that the amount of active substance for wound healing, per cm$^2$, is equivalent to the amount of active substance found in about 10$^3$–10$^7$ of living keratinocytes, preferably in 10$^4$–10$^6$ of living keratinocytes, especially in 5×10$^4$–5×10$^5$ of living keratinocytes. (It is to be understood, of course, that one cannot measure directly how much of the active substance is present in a culture of living cells; thus, the active substance has been described with reference to the amount of active substance present in an amount of keratinocyte cells.)

Examples of types of surface wounds which can be treated with the pharmaceutical composition of this invention include:

thermal, chemical, electrical and radiation-induced burn wounds of skin; burn wounds covered with meshed skin autografts will also benefit from keratinocyte preparations of this invention, which will stimulate the closure of the meshed skin interstices;

full thickness and partial thickness, mechanical wounds such as incisions, abrasions and lacerations; these types of wounds include also surgical and excision wounds in skin;

various ulcerations of skin, such as decubitus, venous and arterial ulcers and ulcers caused by underlying diseases such as diabetes and vasculitis;

corneal wounds;

tympanic membrane lesions; and lesions due to pathological conditions such as bullous pemphigoid, epidermolysis bullosa and lupus erythomatosus.

This invention yet further relates to a process for promoting the healing of a surface wound (for example in skin, e.g., human skin), by applying the pharmaceutical composition of this invention to the surface of the wound.

The invention also relates to a process for preparing a culture of keratinocyte cells free from non-autologous fibroblasts and free from organ extracts, particularly pituitary extracts comprising:

keratinocyte cells seeded on a support at a density as low as 1×10$^4$ cells/cm$^2$, preferably at 3 to 5×10$^4$ cells/cm$^2$ in a culture medium containing a basal medium, itself containing Medium 199, with the following additives: serum, epidermal growth factor (EGF), hydrocortisone and/or cholera toxin, and possibly insulin, free from non-autologous fibroblasts, and free from organ extracts, particularly pituitary extracts; and growing such cells at a temperature of 37° C. in a water-saturated atmosphere containing $CO_2$, preferably in the range of about 1% to about 10%, more particularly in the range of about 2% to about 8%.

To obtain a cell sheet, it is necessary to seed the keratinocytes on a support. The support can be plastic or any natural (e.g., collagen or de-epithelialized dermis), semi-synthetic (e.g., fibronectin-coated plastic) or synthetic support (e.g., polyurethane), allowing cell growth.

In the examples, results are given relative to the role of EGF, cholera toxin, hydrocortisone, and insulin in feeder layer-free keratinocyte growth in vitro.

Medium 199 of this process is disclosed in the Belgian catalogue of Gibco BRL Life Technologies (1991) on page 46. Medium 199 can be replaced by medium CMRL 1066 (Belgian Gibco BRL Life Technologies catalog, page 39, 1991) or by Williams E. Medium (Williams E medium: Belgian Gibco BRL Life Technologies catalog, page 62, 1991) or a combination of both.

Serum of this process contains bovine serum albumin (BSA), but preferably, additional BSA is added such that the total concentration of BSA in the culture medium is no less than about 0.5 g/l. Fetal bovine serum contains 13–29 g serum albumin per liter; hence, for a concentration of 10% fetal bovine serum in 1 liter culture medium, there will be 1.3–2.9 g serum albumin, and in case 1 g bovine serum albumin is added per liter, there will be 2.3 g–3.9 g of serum albumin in 1 l culture medium. In case 10% serum is added to the medium, the additional BSA has little influence.

According to another embodiment of the invention, the culture medium for the process can be modified during the process. For instance, it is possible to use a first culture medium containing cholera toxin as, additive and subsequently to use a second culture medium containing epidermal growth factor, hydrocortisone, and cholera toxin as additives. According to another preferred embodiment of the process, the culture medium contains Medium 199, serum and the following three components: hydrocortisone, epidermal growth factor, and cholera toxin.

The process of the invention and the cultures of the invention have the following advantages:

the cells can be seeded at the same density as in the 3T3 feeder layer systems, the process is easier: it does not require 3T3 cells, which must become growth arrested and then seeded before, or along with, the keratinocytes;

the process is less expensive: to have the 3T3 cells available for a keratinocyte culture, a constant culture of 3T3 cells at an optimal culture density is necessary, demanding additional work, time, and material. Moreover, the 3T3 feeder layer cells have to be growth arrested, e.g., by mitomycin C treatment or γ-irradiation;

the process is free of remaining 3T3 cells: in the classic 3T3 feeder layer technique a wash with EDTA is performed to remove as many remaining 3T3 cells as possible before the keratinocyte sheet is applied on the wound; it cannot be excluded that the 3T3 cells, which remain in the keratinocyte sheet and are in direct contact with the wound bed could, for instance, induce immunologic reactions in the host;

the process is safer: 3T3 cells are infinitely dividing neoplastic cells; even if the cells are γ-irradiated or mitomycin C treated, this process obviously is safer since no 3T3 is added at all;

the process is substantially pure: after skin trypsinization, the epidermis is removed from the dermis, the dermal part is gently scraped only once; by doing so, the keratinocyte cultures are substantially free of fibroblasts; indeed, contaminating fibroblasts prevent the keratinocytes from forming a sheet; other epidermal cells such as Langerhans cells, Merkel cells and melanocytes do not divide under the culture conditions of the invention;

the process provides confluent keratinocyte cultures on short notice: starting from the same amount of isolated keratinocytes, the present cultures reach confluence in about the same time period as cultures with the 3T3 feeder layer; and this feeder layer-free system permits the preparation of keratinocyte sheets which may be used freshly, or are stored in liquid nitrogen until required; the sheets may also be used for preparation of lyophilized keratinocytes or cell extract of the keratinocytes.

The invention also relates to a process wherein the culture medium is such that the basal medium contains:
about 20% to about 100% (w/v) of Medium 199, with said medium being liable to be replaced up to 80%, preferably up to 75%, by another basal culture medium such as MEM medium,
serum in the culture medium is maintained at a concentration of about 2% to about 25%, particularly of about 4% to about 15% (v/v), more particularly 10%, with said serum being preferably fetal serum, or newborn serum, particularly fetal calf serum;
hydrocortisone in the culture medium is maintained at a concentration of 0 to about 4 μg/ml, particularly of about 0.01 μg/ml to about 2 μg/ml, preferably of about 0.1 to about 0.8 μg/ml, more preferably 0.4 μg/ml,
epidermal growth factor in the culture medium is maintained at a concentration of about 1 to about 100 ng/ml, particularly of about 1 to about 50 ng/ml, preferably of about 3.3 to about 20 ng/ml, more preferably 10 ng/ml,
cholera toxin in the culture medium is maintained at a concentration of 0 to about 80 ng/ml, particularly of about 1 to about 50 ng/ml, preferably of about 3 to about 18 ng/ml, more preferably 9 ng/ml,
insulin in the culture medium is maintained at a concentration of 0 to about 30 μg/ml, particularly of about 1 to about 10 μg/ml, for instance 5 μg/ml. The concentration of the basal medium in the culture medium is about 80% to about 98%.

In the basal medium, if there is less than 20% of Medium 199, the growth is likely to be slower and cells support less than 8 passages.

The invention also relates to a process wherein the culture medium is free from bovine brain extract, triiodothyonine, transferrin, human Cohn fraction V, and adenine other than adenine contained in Medium 199.

The invention also relates to a process wherein the culture medium is free from ethanolamine, selenite, putrescine, and phosphoethanolamine.

The invention also relates to a process for preparing a culture of confluent keratinocyte cells wherein the process used is according to the invention and comprises the following steps:
changing the culture medium of the cells at least about every 4 days, preferably after two days, and
stopping the growth of the culture after a time sufficient to obtain a confluent cohesive multilayered culture by placing the cells in a survival medium for a time sufficient for them to reject the above-mentioned additives, with said survival medium being such that the cells can remain alive, but where there is no stimulation for proliferation and differentiation of the cells, with said medium being, for instance, the culture medium according to the invention containing preferably no serum, and preferably no additional BSA, no epidermal growth factor, no hydrocortisone, no cholera toxin and no insulin, or being any other basal medium or a mixture of any basal media; and
washing the cells to remove the above-mentioned survival medium, for instance with PBS.

No stimulation for proliferation means that they can proliferate by themselves but are not externally forced.

An example of a basal medium which is used as a survival medium can be DMEM-F12.

The culture medium is changed every 4 days to replace the nutrients which have been used and to eliminate the metabolites produced by the culture of the cells.

The growth of the culture is stopped generally after about 10 days, preferably 11 days, in order to obtain a confluent cohesive multilayered culture.

The cells are generally placed in a survival medium for about 1 or 2 days, to get rid of the above-mentioned additives. If they are placed for more than 2 days in a survival medium, they can suffer from a lack of nutrients.

When the cells are washed, they are ready for direct use in wounds or for lyophilization or for cryopreservation.

DMEM-F12 is disclosed in the Belgian catalogue Gibco BRL Life Technologies (1991) on page 41.

There is preferably no serum in order to avoid immunological reactions due to the presence of non-human substances.

Preparing Lysate From Keratinocytes not Detached From the Support

The invention also relates to a process for preparing lysed keratinocyte cells wherein the cells are obtained according to the invention but wherein the cells are not removed from the support prior to preparing the lysate. This procedure includes the following steps:
culturing the keratinocytes on a support according to the invention
placing the cells in a survival medium for 1 to 2 days, in which the cells can remain alive but where there is no stimulation of proliferation and differentiation of the cells, with said medium being for instance the culture medium according to the invention but containing preferably no serum and no additional BSA, no epidermal growth factor, no cholera toxin, no hydrocortisone and no insulin, or any other basal medium or mixture of any basal media or being DMEM-F12.
removing said survival medium and washing the cells with a washing medium, for instance with PBS. Preferably, 3 washing cycles are performed. The volume of washing medium in each cycle is preferably about 2–3 times the volume of the culturing medium in which the cells were cultured.
removing the washing medium
inducing cell lysis by placing the cells (still attached to their support) in a hypotonic solution, for instance water or PBS diluted with water or any other hypotonic solution, and leaving this hypotonic solution on the cells for at least 1 minute, preferably about 10 minutes, more preferably about 60 minutes. Preferably, this step is carried out at 2–8° C.

Preparing Keratinocyte Cultures by Growing the Cells Without a Support

The invention also relates to a process for preparing keratinocyte cultures by growing the cells without a support using a procedure comprising the following steps:
keratinocytes are seeded in a culturing vessel in a culturing medium according to the invention, or any other culturing medium allowing keratinocyte proliferation in the absence of fibroblast feeder layers. The density of the seeded cells is preferably about 10–1,000,000 cells/ml, more preferably about 100 to 100,000 cells/ml, more preferably about 1,000–10,000 cells/ml
The culturing vessel can, for instance, be a glass, metal or plastic vessel equipped with a system to agitate the culturing medium. The walls of this culturing vessel may be manufactured from a material to which the cells to not adhere, or alternatively the walls of the vessel may be treated so as to prevent the cells to attach (for instance, treatment with a silicone solution will make the walls sufficiently hydrophobic to prevent cell adhesion). Agitation of the culturing medium can for instance be obtained by a motor-driven propeller or a magnetic spinning bar, by pumping the medium around the vessel, by moving the vessel in such a way as to agitate the medium, by pumping air or another gas through the medium or by any other system known in the art. The degree of agitation of the medium is optimized such as to substantially prevent the cells from attaching themselves to the vessel walls, yet should be sufficiently low such as to prevent cell damage.

An alternative culturing vessel useful for the support-less culturing of keratinocytes is a rotary wall cell culturing system such as marketed by the company Synthecon Inc. (8054 El Rio, Houston, Tex., USA). Basically, such a system, which exists in several versions, consists of a culturing vessel equipped with a gas exchange membrane and filled with culturing medium. This vessel continuously rotates at a certain speed along its longitudinal axis. Because of viscous coupling, the liquid medium within the vessel accelerates until the entire fluid mass inside the vessel rotates at the same angular velocity as the outside wall. This keeps the cells in continuous free fall, thus simulating microgravity conditions. The cells in such a bioreactor rotate as a solid body with minimal disruptive shear. This allows the cells to form clusters and three-dimensional structures without attaching to a support (references to such culturing systems can for instance be found in INVITRO Animal, vol. 33, pp332–398, 1997).

When the keratinocyte cultures have reached a sufficient density, the cells are collected from the culturing vessel, for instance by centrifugation at a speed sufficient to sediment the cells or by filtration over a filter with a pore size suitable to retain the cell but allowing the medium to pass through.

Spray Drying of Keratinocyte Lysate as an Alternative to Lyophilization

The invention also relates to a process of obtaining a dry lysate power by spray-drying the lysate (instead of lyophilising), comprising the following steps:

preparing keratinocyte culture according to the invention preparing a keratinocyte cell lysate from said keratinocyte culture according to the invention preferably adding to the lysate an additive, or mixture of additives. Such additives may include for instance sucrose, trehalose, serum albumin, Carbomer C981, polyvinylpyrrolidone, etc. The function of this additive or mixture thereof is to increase the yield of the spray drying process, to form a suitable powder upon drying and to protect the lysate from heat-induced damage during the process. However, the addition of such compounds is not an absolute necessity and dried lysate is also obtained by spray-drying the lysate in the absence of such compounds. Other additives which can be added include gel-forming agents, such as Carbomers, Pluronics, Hydroxyethylcellulose, methylcellulose, etc. In this case, the spray-dried lysate powder can readily be converted to a hydrogel by hydration with an aqueous solvent. The resulting hydrogel constitutes a useful formulation of the lysate.

Spray drying can be carried out in any spray drying device known in the art, for instance a Buchi type B-191 spray-dryer (Buchi Labortechnik A.G., Switzerland), equipped with an intake air filter and aspirator filter.

Spray drying conditions are optimized so as to maximize the yield of the process, at the same time minimizing damage to the lysate (yield is defined as ((total theoretical dry weight of spray-dried material)-(collected weight of spray-dried material) divided by the total theoretical dry weight of the spray-dried material)). Parameters which are taken into consideration for this optimization include inlet air temperature, lysate pump speed, air flow rate, aspirator speed and nozzle diameter these parameters have to be optimized depending in the particular size and brand of spray-drier used and depending on the concentration of the lysate and additives.

Spray-dried lysate powder is very stable and can be stored for months to years. For use, this spray dried lysate powder can be formulated in any excipient according to the invention.

The invention also relates to a process for preparing a culture of confluent and differentiated keratinocyte cells wherein the process used is in accordance with the invention and comprises the following steps:

changing the culture medium of the cells at least about every 4 days; and stopping the growth of the culture after about 21 days by placing the cells in a survival medium for about 1 to 2 days where the cells can remain alive, but where there is no stimulation for proliferation and differentiation of the cells, with said medium being for instance the culture medium according to the invention containing preferably no serum and no additional BSA, but no epidermal growth factor, no hydrocortisone, no cholera toxin and no insulin, or any other basal medium or a mixture of any basal media or being DMEM-F12; and washing the cells to remove the above-mentioned medium, for instance with PBS.

The invention also relates to a process wherein said cells are recovered in the form of sheets after being detached from the support, for instance by means of Dispase.

The invention also relates to a process for preparing keratinocyte cells in a lyophilized form, wherein the cells, after being obtained according to this invention as described above and then lysed (for instance by means of a hypotonic solution), detached from the support (for instance by mechanical means), collected, and possibly sonicated, are frozen at a temperature from about −20° C. to about −196° C., preferably at about −40° C., and are then lyophilized under vacuum to give a dry substance constituting the lyophilisate. Alternatively, the cells can be first detached from the support (for instance by mechanical means or by treatment with Dispase), subsequently lysed (for instance by means of a hypotonic solution or by sonication) and then lyophilized.

An example of a hypotonic solution can be PBS diluted ten times with water.

The cells can be detached from the support for instance by scraping, for instance with a rubber policeman.

The advantages of sonication is that by breaking the cells open, the cell contents are liberated.

The invention also relates to a process for preparing extracts of keratinocyte cultures, wherein the cells are obtained according to the invention, wherein the cells, after being lysed (for instance by means of hypotonic solution), detached from the support (for instance by mechanical means) and collected, are sonicated and centrifuged to give:

a supernatant containing molecules which are soluble in the hypotonic solution, possibly containing substances which have been detached from the cell membrane by sonication and a pellet containing the cell membrane and nuclei, and wherein the supernatant or the pellet is recovered and possibly frozen and lyophilized.

The technique of the invention for preparing lyophilized material from keratinocyte cultures essentially comprises the steps of:

using primary or passaged, confluent to differentiated keratinocyte cultures, grown feeder-layer free, as source;

rinsing the cultures with PBS, scraping the cells from the culture surface with a rubber policeman, lysis of the cells by hypotonic shock and/or sonication;

lyophilization to obtain total lyophilisate, or preparation of cell fractions by centrifugation; and subsequent lyophilization of the supernatant and pellet fractions.

To obtain sterile extracts, the process can be carried out under sterile conditions. Alternatively, the extracts can be sterilized after lyophilization, for instance by ultraviolet light or gamma ray irradiation. If necessary, the extracts can subsequently be rehydrated and/or reformulated as a gel, creme, ointment, etc, for example by redissolving the extracts in a water-miscible gel or in a salt solution.

The invention also relates to a process for preparing cryopreserved cultures of keratinocytes wherein the cells are obtained according to the invention, and wherein the cells are placed in a cold medium, preferably isotonic and buffered, at a temperature of about 0 to about 15° C., with said medium containing serum preventing the cells from freezing damage and possibly preventing the toxicity of the cryoprotectant which is further added to said cold medium to avoid damaging the cells, and wherein the cells are frozen at a temperature of –20° C. to about –196° C., preferably at –70° C., after which the cells are placed in liquid nitrogen.

In the expression "cold medium", "cold" means that the temperature should be lower than 37° C. and preferably between 0 and 15° C.

An example of such a medium is an isotonic buffered solution and is constituted by any basal medium to which 10% serum and 10% cryoprotectant are added such as DMSO or glycerol or a mixture of DMSO and glycerol.

Cryopreservation in medium without serum results in more freezing damage. If there is no serum, only few viable cells are recovered and the cell sheets will fall into pieces.

The invention also relates to a process for preparing cryopreserved cultures wherein the cells are obtained according to the invention, and comprises the following steps:

changing the culture medium of the cells at least about every 4 days and stopping the growth of the culture after about 21 days by placing the cells in a survival medium where the cells can remain alive, but where there is no stimulation for proliferation and differentiation of the cells, with said medium being, for instance, the culture medium according to the invention containing possibly serum, and possibly additional BSA and insulin, but no epidermal growth factor, no hydrocortisone and no cholera toxin, or any other basal medium or being DMEM-F12, washing the cells to remove the above-mentioned survival medium, for instance with PBS, and recovering the cells in the form of sheets which are detached from the culture support and wherein the sheets of cells are placed in a cold medium, preferably isotonic and buffered, at a temperature of about 0° C. to about 15° C., with said medium containing serum preventing the cells from freezing damage and possibly preventing the toxicity of the cryoprotectant which is further added to said cold medium from damaging the cells and the sheets of cells, and wherein the sheets of cells are frozen at a temperature of –20° C. to about –196° C., preferably at –70° C.

The sheets of cells are then placed in liquid nitrogen.

The invention also relates to a culture medium containing a basal medium, itself containing Medium 199, with the following additives: serum, epidermal growth factor, cholera toxin and/or hydrocortisone, and possibly insulin, and free from non-autologous fibroblasts and free from organ extracts, particularly pituitary extracts.

The invention also relates to a medium culture containing Medium 199 as basal medium and as additives: serum, and at least two of the following three components hydrocortisone, epidermal growth factor, cholera toxin, and possibly insulin.

The invention also relates to a culture medium containing a basal medium, itself containing Medium 199, serum and the following components: hydrocortisone, epidermal growth factor, and cholera toxin, and possibly insulin.

A preferred medium of the invention contains:

about 20% to about 100% (w/v) of Medium 199, with said medium being liable to be replaced up to 80%, and preferably up to 75%, by any other basal culture medium such as medium MEM, serum in the culture medium is contained at a concentration of about 2% to about 25%, particularly at about 4% to about 15% (v/v), more preferably 10%, with said serum being preferably fetal serum, or newborn serum, particularly fetal calf serum, hydrocortisone in the culture medium is contained at a concentration of 0 to about 4 µg/ml, particularly of about 0.01 to about 2 µg/ml, preferably of about 0.1 to about 0.8 µg/ml, more preferably 0.4 µg/ml, epidermal growth factor in the culture medium is contained at a concentration of about 1 to about 100 ng/ml, particularly of about 1 to about 50 ng/ml, preferably of about 3.3 to about 20 ng/ml, more preferably 10 ng/ml, cholera toxin in the culture medium is contained at a concentration of 0 to about 80 ng/ml, particularly of about about 1 to about 50 ng/ml, preferably of about 3 to about 18 ng/ml, more preferably 9 ng/ml, insulin in the culture medium is contained at a concentration of 0 to about 30 µg/ml, particularly of about 1 to about 10 µg/ml, for instance 5 µg/ml.

The cultures of keratinocytes of the invention present wound healing properties.

Stimulation of keratinocyte proliferation in vitro is one property of the keratinocyte-derived preparation. However, it is not excluded that a minor amount of inhibitors may be present.

Investigations have been carried out on a animal model. Full-thickness wounds were treated with renaturated lyophilized keratinocyte substances (i.e. total lyophilisate and cell extracts), classic wound treatment, and application of the known growth factor TGF-α, which may be produced by cultures keratinocytes. Full-thickness wounds, extending into the hypodermis, are among the most difficult to heal.

The stimulating activity of keratinocyte material on epithelial cell growth is known. However, it is not clear whether cultured keratinocytes contain substances that may inhibit certain phases of the wound healing process. This can be elucidated in full-thickness wounds.

Rigorously defined criteria were used to describe the wound healing clinically and histologically. An important criterium is the time required for wound closure. Moreover, the quality of the healed skin is of paramount importance. The more the scar tissue resembles unwounded skin histologically, the better the quality. It can be concluded that the keratinocyte-derived substances of the invention contain wound healing activity. Total lyophilisate resulted in rapid healing and a qualitatively better scar, compared with the controls and with the effect of fresh or cryopreserved keratinocyte sheets, TGF-β, and classic treatment with Duoderm®.

EXAMPLE 1

Skin Source and Isolation of Keratinocytes

Human keratinocytes were isolated from surgical skin specimens (foreskin, mammoplasties, abdominal skin, and other locations on the body), and from cadaver skin.

Skin was removed with a dermatome at a thickness up to 1 mm. Thicker pieces of skin, sometimes containing hypodermis, were used as well. The skin was immediately placed in phosphate buffered saline (PBS): 8 g NaCl, 0.2 g KCl, 3.1 g $Na_2HPO_4.12H_2O$, 0.2 g $KH_2PO_4$ in MILLI-Q® water to 1 L; pH 7.4) and kept at 4° C. Specimens were then transferred to the culture lab within 4 h. The skin was rinsed extensively with PBS containing 100 U/ml penicillin, and 100 mg/ml streptomycin. If necessary, skin samples were stored at 4° C. in solution A, which is an isotonic buffered solution containing 30 mM Hepes, 10 mM glucose, 3 mM KCl, 130 mM NaCl, 1 mM $Na_2HPO_4.12H_2O$ and 3.3 nM phenol red. Thin pieces of skin may be stored for about 16 h, thicker pieces for about 4 days.

Fat tissue was removed as much as possible. The skin was cut into smaller pieces of approximately 0.5×0.5 cm and floated in trypsin solution (0.25% trypsin Sigma in Solution A). The procedure depends on the thickness of the skin sample. Thin meshed skin was trypsinized for about 20 min at 37° C., while thick skin was trypsinized for about 16 h at 4° C.

The epidermis was removed from the dermis by using forceps. The epidermis was then suspended by up-and-down pipetting and passaging through an injection needle (21 G, 0.8×50). An alternative procedure was to scrape the basal side of the removed epidermis in order to collect the basal cells. The remaining suprabasal epidermal tissue is discarded. The upper part of the dermis still contained numerous basal keratinocytes but also fibroblasts and was therefore gently scraped, but only once. The trypsinization was stopped by addition of 10% fetal calf serum. The cell suspension was then filtered through sterile gauze (Perlon P6, 63 mm) and centrifuged at low speed (120 g for 8 min).

Cell Counting Urns

The 0.2-ml cell suspension was mixed with 0.1-ml trypan blue solution (0.4% in 0.85% saline; Flow Laboratories). About 3 min later the cells were counted in a hemocytometer (Neubauer chamber). Blue-stained cells are dead, while unstained cells are viable.

Culture of Human Keratinocytes

The cells were resuspended in culture medium and seeded in a plastic petri dish (100 mm diameter, Becton Dickinson) at a density of $5 \times 10^4$ viable cells/cm². The cells were grown in an incubator at 37° C. in a water-saturated atmosphere with 5% $CO_2$ in air.

One liter of culture medium (pH=6.9–7.4, preferably= 7.1), consisted of 2.78 g Medium 199 (Gibco; with Hank's salts, with glutamine, without $NaHCO_3$), 8.03 g Minimal Essential Medium (Gibco; with Hank's salts, with glutamine, without $NaHCO_3$), 1.3 g $NaHCO_3$ (Sigma), 1 g bovine albumin (Sigma), 5 mg insulin from bovine pancreas (Sigma), 50 mg glutamine (Sigma), 9 μg cholera toxin (Sigma), 100 mg streptomycin sulfate (Gibco), 100,000 U penicillin (Gibco), 10 μg epidermal growth factor (Gibco), 0.4 mg hydrocortisone (Sigma), and 10% heat-inactivated fetal calf serum (56° C., 30 min) (Gibco). The medium was prepared in Milli-Q water (Millipore) and sterilized by filtration (Millipore).

Culture medium is changed 3 days later and subsequently every 2 to 3 days. The culture was confluent after 10–16 days. Thicker sheets, containing 3–5 cell layers, were considered to be differentiated and were obtained after about 20 days of culture. Pig keratinocytes were isolated and cultured by the same technique.

Subculture

The subconfluent keratinocyte culture was rinsed three times with PBS and covered with trypsin (0.05%) and EDTA (0.02%) in modified Puck's saline (Gibco). When the cells were detached, they were collected and centrifuged at 120 g for 8 min. The pelleted cells are resuspended in culture medium. The split ratio is 1:3.

Preparation of Total Lyophilisate and Cell Extracts

Subconfluent, confluent, and differentiated cultures were used as source. Twenty-four hours before the cultures was stopped, the culture was rinsed 3–4 times with PBS, and DMEM/F12 (Gibco) added without additives or fetal calf serum. The next day, the cultures were washed twice with PBS and the dish was covered with 5 ml sterile 1/10 PBS (PBS diluted 10 times with MILLI-Q® water). Five minutes later, the cells were scraped with a rubber policeman and collected in a 50 ml Falcon tube (Becton Dickinson). The dish was rinsed twice with 5 ml 1/10 PBS in total. This solution was added to the Falcon tube. The tube was gently shaken for about 5 minutes and frozen at −30° C. The samples were lyophilized within 24 h. Lyophilized material was stored in the Falcon tube at −30° C.

Cell extract was prepared from the same source of cultured keratinocytes. The cells were scraped with a rubber policeman in PBS or hypotonic PBS (1/10 PBS in MILLI-Q® water). The suspension was sonicated (15 sec, 3 times) or ultra turraxed (13,500 rpm, 3 times 15 sec in ice bath); Ultra-turrax T25® Janke & Kunkel, IKA, Laborcechnik, Germany) and subsequently centrifuged at 10,000 g for 30 min at 4° C. The resulting supernatant and pellet were lyophilized separately and stored at −30° C.

Treatment of the culture keratinocytes with Dispase (12 U per petri dish of 10 cm diameter for about 15 min at 37° C.; Boehringer) followed by 3 washes with PBS was an additional step which may be introduced before the cells are scraped from the dish. Such treatment does not, influence the activity of keratinocytes.

The lyophilisate was sterilized under bactericidal ultraviolet light (15 min, at a distance of about 50 cm from the light source).

Preparation of the Gel 0.2 g IDRORAMNOSAN® (Federa, Brussels) was dissolved in 10 ml 0.9% NaCl or in Milli-Q water. Sterilization was performed by autoclaving 40 min at 120° C.

Redissolving the Lyophilized Substance

Prior to application on a wound the lyophilized substance was, rehydrated and/or redissolved. The amount of sterilized cultured keratinocytes obtained from one petri dish was mixed in a sterile manner with 1.5 ml of the gel, before application on the wound.

Animal Model for Wound Healing

The goal of the in vivo experiments was to find out whether lyophilized keratinocyte-derived material contains wound healing activity and whether this activity was better than that obtained with fresh keratinocyte sheets, cryopreserved keratinocyte sheets, classic wound treatment with DUODERM® (ConvaTec Squibb) or TGF-α, which is a known keratinocyte growth factor. The lyophilized keratinocyte material was rehydrated in a gel before application.

The domestic swine was chosen as experimental animal since the histological characteristics of its skin are similar to that of human skin; examples include the relative thickness of the epidermis and dermis, the relative sparcity of hair, and the presence of subcutaneous adipose tissue.

Young adult male and female pigs, weighing about 60 kg, were pretreated with STRESNIL® (intramuscular, 40 mg/20 kg; Janssen), anesthetized with HYPNODIL® (intravenous, 75 mg/20 kg; Janssen) and kept under anesthesia with FLUOTHANE® (ICI). After shaving the back, the skin was disinfected with HIBISCRUB® (ICI) and ISOBETADINE DERMICUM® (Asta Medica, Brussels). Surgical wounds, 3×3 cm, were induced on the back close to the spine. The distance between the wound edges was 5 cm. One row of 6 wounds was made on the left side, and one row of 6 on the right of the spine. The wounds were treated with the substances listed below, covered with occlusive dressing (TEGADERM® 3M or OPSITE® Smith and Nephew), and fixed with FIXOMULL® (Beiersdorf) dressing. Finally, the trunk was wrapped with an elastic nonadhesive bandage. The pig was allowed to recover in his sty. The wounds were inspected every 4 to 5 days. New material was applied and dressings are changed until the wounds are closed, which took about three weeks. The animal receives normal food pellets and water ad libitum.

Experiments were performed on 4 animals. The unit of application of keratinocyte-derived material is the amount obtained from 1 petri dish of 10 cm diameter.

The following substances were tested for wound healing activity:
  DUODERM®, which is one of the most frequently used wound covering substances (assayed in animal No. I, II, III, and IV);
  fresh, differentiated keratinocyte sheets, obtained about 20 days after culture (No. I, II, III, and IV). The sheets were applied with the keratinocytes facing downwards on the wound;
  cryopreserved differentiated keratinocyte sheets were cultured and detached approximately 20 days after seeding and stored in liquid nitrogen (No. I, II, III, and IV). The sheets were put on the wound with basal keratinocytes facing downwards;
  lyophilized keratinocytes were prepared starting from keratinocyte sheets which were collected in 1/10 PBS and lyophilized (No. I, II, III, and IV);
  10,000 g supernatant were derived from keratinocyte cultures, which were lysed in 1/10 PBS, homogenized in an ULTRA-TURRAX® Janke & Kunkel, IKA, Labortechnik, Germany) and centrifuged at 10,000 g for 30 min (No. I, II, III, and IV). The 10,000 g supernatant was applied at different concentrations varying between 3×concentrated to a 1/500 dilution (No. I and II);
  the 10,000 g pellet was the 10,000 g sediment of the described procedure (No. I, II, III, and IV);
  TGF-α is one of the factors which may play a role in wound healing. Four hundred ng, dissolved in 1.5 ml gel, was applied per wound (No. I, II, III, and IV);
  gel is 1.5 ml gel in which dry substances, such as lyophilized keratinocytes or TGF-α, were dissolved before application on the wound (No. I, II, III, and IV);
  the control wound was treated with saline only.

Several criteria were defined, allowing macroscopic and microscopic evaluation of the healing wounds. These aspects, which are studied at a certain time point, are marked with an asterisk in Tables 1 and 2. The evaluation was performed independently by 3 investigators. The final result was obtained upon agreement of all 3.

TABLE 1

Criteria for the macroscopic evaluation of healing wounds at different time points after wounding

|  | before closure | at closure | about 2.5 months after closure |
|---|---|---|---|
| wound depth (deep, superficial, equal) | * | | |
| granulation tissue | * | | |
| edge effect | * | | |
| crust formation | * | * | |
| presence of fibrin-like membrane | * | | |
| evenness of the scar | | * | * |
| contraction (one/two directions, none) | * | * | * |
| scale formation | | * | * |
| epithelialization/closed | | * | |
| worst wound appearance | | * | |
| aspect (opaque, lucent, erythema | | * | * |

For the microscopic evaluation, punch biopsies (3 mm diameter) were taken at the moment of wound closure and about 3 months after wound induction, i.e., at 105 days in the second animal, and at 84 and 91 days in the third and fourth animal, respectively. Each time 2 sets of punch biopsies (3 mm diameter) were taken, one for fixation in formol and one for freezing. Paraffin sections were prepared from the formol-fixed biopsies and subsequently stained with routine hematoxylin-eosin or specific stainings. Specific stainings were used for revealing the basement membrane, melanocytes, reticulin, and elastin. Cryostat sections were made from the frozen samples and used for immunocytochemical experiments, investigating the presence of certain keratins, Langerhans cells, and blood capillaries.

Wound closure was defined as epithelialization observed macroscopically. The time point of 23 days (see below) was chosen arbitrarily as a reference point for 2 reasons: (i) the experiment with the first animal had to be stopped at 23 days, and (ii) most wounds closed in the animals at 23 days.

TABLE 2

Criteria for the evaluation at the microscopic level of healing wounds at different time intervals.

|  | at closure | about 2.5 months after closure |
|---|---|---|
| EPIDERMIS | | |
| epidermis attached/detached | * | * |
| rete ridges (number, penetration, size) | * | * |
| thickness (basale + spinosum + granulosum) | * | * |
| position of the nuclei in the basale | * | * |
| number of cell layers in the granulosum | * | * |

TABLE 2-continued

Criteria for the evaluation at the microscopic level
of healing wounds at different time intervals.

|  | at closure | about 2.5 months after closure |
|---|---|---|
| parakeratosis | * | * |
| aspect of the corneum | * | * |
| presence of melanocytes (Fontana staining) |  | * |
| presence of Langerhans cells (enzyme cytochemistry, immunocytochemistry) |  | * |
| cytokeratin (8,18,19; 10,11; 13, 16*) |  | * |
| DERMIS |  |  |
| blood vessels (number, size, open/closed, orientation) | * | * |
| capillaries in the papillare (amount, organization) (factor 8 immunocytochemistry) |  | * |
| presence of hair follicles and sweat glands | * | * |
| collagen fibers/bundles (orientation, size, amount, localization) | * | * |
| basement membrane (PAS staining) |  | * |
| elastin (orceine staining) |  | * |
| reticulin (silver impregnation) |  | * |

(*) numbers refer to cytokeratin types

Since (i) contraction was small at the moment of closure (ii) the wounds with the largest contraction did not close first, and (iii) wounds which were closed first did not show great contraction, it was concluded that, in our model, closure was not due to wound contraction but to epithelialization. The position of the wound affects the direction and extent of contraction. In general, all scars were scaly after closure and several weeks later. Hypertrophic scars were not seen at 2.5 months after closure, i.e., the end of the experiments.

For the microscopic criteria the histology of unwounded skin served as a reference. Microscopic observation of the scar tissue provided important information on the quality of the scar. No evidence was found that the location of the wound influenced the histology of the healing wound. Thus, the quality of the scar was mainly influenced by the substance used for wound treatment. However, large histological differences between animals were seen. It is likely that these differences were due to interanimal differences. For instance, DUODERM®, which has a constant quality, was applied to the wound in the neck of all 4 animals, and resulted in different histology. Interanimal differences were observed using keratinocyte-derived substances as well. For instance, following application of keratinocyte sheets or lyophilized keratinocytes, more pronounced rete ridges were found at the time the wounds were closed in animals No. I and II than in No. III and IV. This may in part be due to the fact that the third and fourth animals originated from a different supplier than the first two pigs.

At the time of wound closure, an irregular hyperplasia was usually observed, i.e., the epithelium was thicker than in unwounded skin. Generally, the epidermis was thinner about 2 months later, but still slightly thicker than normal epithelium.

The quality of the scar at a later time is of great importance. Attachment of the epidermis to the dermis and the presence of true rete ridges are important criteria for evaluating the quality of scar tissue. A tendency exists to normalize the size and number of rete ridges as a function of time. Indeed, when there were no or few ridges at closure, the ridges were more numerous and better developed at 3 months on the other hand, when the ridges were much larger after closure than in normal skin, these structures tended to be more normal at 3 months.

Table 3 summarizes the results relative to the number of days necessary for the wound closure.

The numbers 1, 2, 3, and 4 correspond to 4 different pigs. In the first column, the product which has been applied on the wound is indicated.

In this table,
  "untreated" corresponds to animals on whose wounds only physiological saline solution was applied;
  "gel alone" corresponds to the case where physiological saline solution was applied on the wounds in the form of a gel;
  "fresh KC" corresponds to fresh keratinocyte cells cultivated according to the invention;
  "cryo KC" corresponds to cryopreserved keratinocyte cells cultivated according to the invention;
  "lyophil" corresponds to lyophilisate of the keratinocyte cells of the invention;
  "10,000 pel" corresponds to the pellets obtained after centrifugation at 10000 g;
  "10,000 su" corresponds to the supernatant obtained after centrifugation at 10,000 g.

TABLE 3

|  | animal number | | | |
|---|---|---|---|---|
|  | I | II | III | IV |
| untreated | after 23 | 22 | after 25 | 17 |
| gel alone | after 23 | after 25 | 22 | 22 |
| duoderm | 18 | after 25 | 18, af. 25 | 17,22 |
| fresh KC | after 23 | after 25 | 22 | 17 |
| cryo KC | 23 | after 25 | 22 | 17 |
| lyophil | 23 | 18 | 18 | 17 |
| 10000 pel | after 23 | after 25 | 18 | 17 |
| 10000 su | after 23 | 22 | 18 | 17 |
| TGF-α | after 23 | 18 | 25 | 17 |

After treatment with differentiated fresh keratinocyte sheets, the wounds closed earlier than 23 days in 2 animals. At the microscopic level, the epidermis was attached to the dermis in all specimens. True rete ridges occurred in 3 of the 7 scars. Two months after closure, the epidermis was attached to the dermis in all 3 scars.

Treatment of wounds with cryopreserved differentiated keratinocyte sheets gave less satisfactory results than the use of differentiated fresh sheets. The wound in animal No. I appeared not to be epithelialized, although macroscopically it seemed closed. The epithelium was detached in 2 of the 3 animals at about 3 months after wounding. Rete ridges were present in 3 of the 7 scars. Parakeratosis occurred in 2 of the 3 scars early after closure.

Wounds treated with lyophilized keratinocytes obtained from differentiated keratinocyte sheets were closed in 3 pigs earlier than 23 days after wound induction. Histologic observation showed that at the time of biopsy, all wounds were epithelialized. The epidermis was attached to the dermis in all sections, except in the biopsy of animal No. II at 105 days, where the epithelium was partly detached. Four of the 7 scars showed true rete ridges. Slight hypergranulosis was seen in the second and third animals at 3 months after wounding.

Covering with DUODERM® resulted in wound closure in 3 animals earlier than 23 days as judged macroscopically.

Few or no rete ridges were seen in animals No. II and III at early and later time points, and in No. IV at 27 days. Thus, epidermal extensions were present in only 3 of 11 scars. The epidermis of all four scars of No. III was not fully attached. At 3 months following wounding, the epidermis was attached in animal No. IV only, i.e. 2 scars out of 5.

The untreated wounds were closed earlier than 23 days in animals No. II and IV. Rete ridges were found in only 2 of 7 scars. Similar results were obtained after application of the gel alone. These scars were of lesser quality than scars following wound treatment with keratinocyte-derived substances.

Upon treatment with 10,000 g supernatant of lysed keratinocytes, wound closure earlier than 23 days was seen in 2 animals. The epidermis was attached in 3 of the 4 scars early after closure, and in 2 out of the 3 scars 2.5 months later. Rete ridges occurred in 4 of 6 scars. The experiments using different concentrations of the supernatant revealed that, at closure, there was no obvious histologic difference between the concentrations used, i.e., varying between 3 times concentrated to a 1/500 dilution.

Application of the 10,000 g pellet of lysed keratinocyte resulted in wound closure earlier than 23 days in 2 of the 4 animals. The epidermis was attached to the dermis in 4 of the 7 scars. True rete ridges were not found. Parakeratosis was observed in 2 of the 3 scars early after closure. Thus, the use of the 10000 g pellet material resulted in scars of lesser quality than after application of the 10,000 g supernatant. Presumably, the amount of active substance is lower in the pellet than in the 10,000 g supernatant, resulting in less satisfactory healing.

The TGF-α wounds in animals No. II and IV closed in less than 23 days. Microscopic observation revealed that no or few rete ridges were present, except in animal No. I at the time of wound closure. Psoriasiform hyperplasia was found in the latter animal. At 3 months following wounding, the epidermis was attached to the dermis in 2 of the 3 scars. Since the healing after application of total keratinocyte lyophilisate is better than after application of purified TGF-α alone, it can be concluded that the healing activity in the lyophilized keratinocyte is not due to TGF-α or at least not to TGF-α alone.

Hair follicles and sweat glands were never found in the scars.

Not all scars were investigated for the presence of specific skin components such as melanocytes, Langerhans cells, Merkel cells, cytokeratin, basement membrane, reticulin, and elastin. The structures were studied in the most representative scars only, i.e. fresh and cryopreserved keratinocyte sheets, lyophilized keratinocytes, Duoderm, gel alone as control, and evidently, unwounded skin. Thus, the scars obtained after wound treatment with lyophilized keratinocyte extracts were not studied here.

The keratin pattern in the scars was similar to that in unwounded skin. The antibody to keratins 10/11 gave a positive reaction, while keratins 8/18/19 were not found. Surprisingly, a positive reaction was seen using the antibody to keratins 13/16. These keratins do not occur in normal human skin, but apparently (at least one of both, presumably keratin 16) are present in unwounded pig skin and in the scars.

We have not observed melanocytes (stained by the Fontana technique) either in the unwounded skin, or in the epithelium of the scars. So far, Langerhans cells have not been detected, in either unwounded skin or in scars by the use of peroxidase enzyme cytochemistry or immunochemistry (anti-human Langerhans antibody OKT6). Merkel cells were not found in pig skin or in the scars (no positivity for keratins 8,18,19).

The basement membrane (revealed by periodic acid Schiff staining) plays an important role in the attachment of the epithelium to the connective tissue of the dermis. The basement membrane was well developed in the healed wounds treated with cultured keratinocytes (fresh sheets, cryopreserved sheets and lyophilized keratinocytes). This was not the case following application of Duoderm or in the controls.

The reticulin pattern (demonstrated by silver impregnation) was similar to unwounded skin. Thin fibers of elastin (revealed by orceine staining) were only found in the scars after application of fresh keratinocyte sheets and lyophilized keratinocytes, but not following wound treatment with cryopreserved sheets, Duoderm, or gel alone.

In conclusion, lyophilized cultured keratinocytes clearly demonstrates more wound healing activity than any other of the tested substances including fresh cultured keratinocyte sheets. The scar is closed more rapidly and the quality is better.

EXAMPLE II

Role of EGF, Cholera Toxin, Hydrocortisone, and Insulin in Feeder Layer-free Keratinocyte Grown In Vitro Summary Epidermal growth factor (EGF) is necessary to induce rapid proliferation of human keratinocytes. However, a low yield of attached keratinocytes is seen when EGF alone is present in the medium. Cholera toxin (CT) allows a high yield of attached and spread keratinocytes. On the other hand, growth arrest is seen when CT alone is present in the culture medium.

Hydrocortisone induces keratinocyte proliferation but is less potent than EGF. Insulin has a beneficial effect on keratinocytes, although its effect is more important when the medium contains EGF and cholera toxin, or EGF and hydrocortisone, than when EGF, cholera toxin, and hydrocortisone are present, particularly at the preferred concentrations.

The optimal concentrations of EGF, hydrocortisone, and cholera toxin in the culture medium are respectively for instance 10 ng, 0.13 μg and 9 ng per ml. Insulin may be added, preferentially at a concentration of 5 μg/ml.

Tests have been carried out to investigate
  the influence of epidermal growth factor (EGF), cholera toxin and hydrocortisone (HY) in the presence of insulin on the growth, and on the attachment and growth of primary (P0) and subcultured (P1) human keratinocytes in comparison with medium containing all 3 or none of the 3 additives
  the influence of EGF+CT, EGF+HY and HY+CT for the same phenomena
  the effect of lowering and increasing the concentration of one additive (EGF, CT or HY), with the other 2 at the "standard" concentration
  the role of insulin in the attachment and growth of human primary keratinocytes.

The complete culture medium contained 10 ng EGF, 9 ng cholera toxin, 0.4 μg hydrocortisone, and 5 μg insulin per ml. All experiments were performed in 6-well plates. As interdonor differences may occur, and in order to circumvent interplate variation, each plate contained 2 internal standards: one where the cells were grown in complete medium, one in medium without all additives.

In order to investigate the effect on cell growth, the cells were seeded in complete medium. Two days later, the cultures were rinsed 3 times with PBS and covered with the specific medium.

Keratinocytes were seeded in the specific medium for examination of the effect of the additives on cell attachment, spreading and growth. In case subcultured (P1) keratinocytes (KC) were used, the cells were grown in complete medium before trypsinization and passage.

CONCLUSIONS

A. Effect of EGP, CT and KY on Cultures Containing Insulin

A.1. EGF:

EGF alone in the medium allowed confluency, although slower when the cells were seeded in this specific medium. This may be due to the fact that a lower yield of attached cells is found when only EGF is present in the seeding medium.

Moreover, the experiments clearly showed that, between EGF, HY, CT and insulin, EGF is the most potent stimulator of keratinocyte proliferation. The combination of HY+CT gave slower growth than EGF+CT+HY, EGF+CT, EGF+HY and than EGF alone, proving that EGF is necessary for rapid growth. The fact that CT+HY+1/3 EGF and CT+HY+2× EGF resulted in slightly slower growth of P0 (primary) and P1 (first subculture) keratinocytes than the complete medium may suggest that the optimal concentration of EGF for this combination of additives is around 10 ng/ml. In the attachment-growth experiments, the effect of CT+HY+1/3 EGF, CT+HY+2×EGF, and complete medium were similar.

When EGF (with or without HY) was present in the medium in the absence of CT, large, flat translucent dividing keratinocytes appeared. Such cells were not observed when CT was present in the culture. However, when the culture reached confluency, such cells were no longer seen (when there is EGF, possibly HY and no CT).

All cells presented the typical keratinocyte morphology and formed multilayer.

A.2. Cholera Toxin:

Confluency was seldomly obtained when CT alone was present in the medium. Apparently confluency may sometimes be reached when primary keratinocytes are seeded in this specific medium. CT allowed a higher yield of attached and spread keratinocytes, as compared with HY and EGF alone in the medium. However, after few days growth arrest occurred. The fact that confluency may be obtained when primary keratinocytes were seeded in medium without EGF+HY+CT, but not when CT alone is present, indicates the proliferation "inhibiting" effect of CT. The combination of EGF+HY gave similar results for the growth of keratinocytes, as compared with EGF+HY+1/3 CT and may be somewhat faster than EGF+HY=2 +CT. The attachment-growth experiments showed that EGF+HY was sometimes slower than when 1×, 1/3 or 2×CT was added to that combination. Regarding the growth of keratinocytes, 1/3CT+EGF+HY and complete medium (=EGF+HY+CT) were slightly faster than 2×CT+EGF+HY, suggesting again that CT may hamper the proliferation of keratinocytes. Thus, the beneficial effect of CT essentially involves improving the yield of attachment. Therefore, the culture medium preferably contains CT. There was no difference between EGF+CT+HY, 1/3 CT+HY+EGF and 2×CT+EGF+HY in the attachment-growth experiments. The optimal concentration of CT may thus be about 9 ng/ml in combination with EGF and HY.

A.3. Hydrocortisone:

Medium containing HY alone as additive gave confluency in certain cultures. A lower yield of attached cells was found when HY alone was present. However, the fact that confluency may be obtained shows that, unlike in the case of CT, there is no growth arrest. Presumably HY induces a slight growth stimulation, since cultures attain confluency by CT+HY, but not with CT alone. Confluency is reached with EGF+CT without HY, but sometimes at a later time point than when HY is also present. Moreover, 1/3 HY+EGF+CT and 2×HY+EGF+CT gave similar results as did HY+EGF+CT in all experiments. Thus, it is advisable to add HY to the medium, although the concentration may be lowered to 0.13 μg/ml without a negative effect on attachment-growth and growth only.

The combination of the three additives EGF, HY and CT gives the best results. However, the attachment-growth experiments showed that the concentration of one factor may vary between: 1/3 to 2× (tested range) the standard concentration, provided that the two other factors have the standard concentration.

B. Effect of Insulin

Growing keratinocytes in medium in the absence of EGF+HY+CT is unsuccessful, except in certain cases where primary cells were seeded in this medium lacking EGF+HY+CT. Moreover, when insulin is also omitted, no confluency could be reached with primary keratinocytes seeded in that medium (table 8). Thus, insulin is beneficial for attachment-spreading-growth of keratinocytes. However, the combination EGF+HY+CT is sufficient to obtain confluent primary cultures.

What is claimed is:

1. A non-viable total keratinocyte lysate obtained by a process consisting essentially of:
   (a) growing unsupported keratinocyte cells;
   (b) lysing said keratinocyte cells to convert the keratinocyte cells to a non-viable total keratinocyte lysate; and
   (c) collecting said non-viable total keratinocyte lysate, wherein said non-viable total keratinocyte lysate promotes healing of a wound.

2. The lysate of claim 1, said process of obtaining the lysate further consisting essentially of
   (d) freezing said non-viable total keratinocyte lysate obtained in (c) at a temperature from about −20° C. to about −196° C. to obtain a frozen lysate; and
   (e) lyophilizing said frozen lysate under vacuum to give a lyophilized non-viable total keratinocyte lysate, wherein said non-viable total keratinocyte lysate promotes healing of a wound.

3. The lysate of claim 1, said process of obtaining the lysate further consisting essentially of spray drying the non-viable total keratinocyte lysate to obtain a spray dried non-viable total keratinocyte lysate.

4. The lysate of claim 3, said process of obtaining the lysate further consisting essentially of adding to the total lysate an additive effective to increase yield of the drying or gel-forming agent.

5. A pharmaceutical composition to promote the healing of a wound, wherein said composition comprises a non-viable ,total keratinocyte lysate according to claim 1 and a pharmaceutically acceptable vehicle.

6. The pharmaceutical composition according to claim 5, wherein said pharmaceutically acceptable vehicle comprises a dry powder, a suspension, or a solution.

7. The pharmaceutical composition according to claim 5, wherein said pharmaceutically acceptable vehicle comprises a gel.

8. The pharmaceutical composition according to claim 5, wherein said pharmaceutically acceptable vehicle comprises a cream.

9. The pharmaceutical composition according to claim 5, wherein said pharmaceutically acceptable vehicle comprises an ointment.

10. The pharmaceutical composition according to claim 5, wherein said pharmaceutically acceptable vehicle comprises a biocompatible matrix other than a gel.

11. A process for treating a surface wound to promote healing in a mammal comprising:

(a) applying to said surface wound the pharmaceutical composition of claim 5; and (b) promoting healing of said surface wound.

12. A non-viable total keratinocyte cell culture lyophilisate obtained by a process consisting essentially of:

(a) growing unsupported keratinocyte cells;

(b) collecting said keratinocyte cells;

(c) freezing said collected keratinocyte cells at a temperature from about −20° C. to about −196° C.; and (d) lyophilizing said frozen cells under vacuum to give a non-viable total keratinocyte cell culture lyophilisate, wherein said non-viable total keratinocyte cell culture lyophilisate promotes healing of a wound.

13. A pharmaceutical composition to promote the healing of a wound, wherein said composition comprises a non-viable total keratinocyte cell culture lyophilisate according to claim 12 and a pharmaceutically acceptable vehicle.

14. The pharmaceutical composition according to claim 13, wherein said pharmaceutically acceptable vehicle comprises a dry powder, a suspension, or a solution.

15. The pharmaceutical composition according to claim 13, wherein said pharmaceutically acceptable vehicle comprises a gel.

16. The pharmaceutical composition according to claim 13, wherein said pharmaceutically acceptable vehicle comprises a cream.

17. The pharmaceutical composition according to claim 13, wherein said pharmaceutically acceptable vehicle comprises an ointment.

18. The pharmaceutical composition according to claim 13, wherein said pharmaceutically acceptable vehicle comprises a biocompatible matrix other than a gel.

19. A process for treating a surface wound to promote healing in a mammal comprising:

(a) applying to said surface wound the pharmaceutical composition of claim 13; and (b) promoting healing of said surface wound.

20. A spray dried non-viable total keratinocyte cell composition obtained by a process consisting essentially of:

(a) growing unsupported keratinocyte cells;

(b) collecting said keratinocyte cells; and (c) spray drying said collected keratinocyte cells to obtain a spray dried non-viable total keratinocyte cell composition;

wherein said spray dried non-viable total keratinocyte cell composition promotes healing of a wound.

21. A pharmaceutical composition to promote the healing of a wound, wherein said composition comprises a spray dried non-viable total keratinocyte cell composition according to claimed a pharmaceutically acceptable vehicle.

22. The pharmaceutical composition according to claim 21, wherein said pharmaceutically acceptable vehicle comprises a dry powder, a suspension, or a solution.

23. The pharmaceutical composition according to claim 21, wherein said pharmaceutically acceptable vehicle comprises a gel.

24. The pharmaceutical composition according to claim 21, wherein said pharmaceutically acceptable vehicle comprises a cream.

25. The pharmaceutical composition according to claim 21, wherein said pharmaceutically acceptable vehicle comprises an ointment.

26. The pharmaceutical composition according to claim 21, wherein said pharmaceutically acceptable vehicle comprises a biocompatible matrix other than a gel.

27. A process for treating a surface wound to promote healing in a mammal comprising:

(a) applying to said surface wound the pharmaceutical composition of claim 21; and (b) promoting healing of said surface wound.

* * * * *